United States Patent [19]

Battilotti et al.

[11] Patent Number: 5,130,265
[45] Date of Patent: Jul. 14, 1992

[54] PROCESS FOR OBTAINING A MULTIFUNCTIONAL, ION-SELECTIVE-MEMBRANE SENSOR USING A SILOXANIC PREPOLYMER

[75] Inventors: Massimo Battilotti, Tor De' Cenci; Giuseppina Mazzamurro, Rome; Matteo Giongo, Capena, all of Italy

[73] Assignee: Eniricerche S.p.A., Milan, Italy

[21] Appl. No.: 454,512

[22] Filed: Dec. 21, 1989

[30] Foreign Application Priority Data

Dec. 23, 1988 [IT] Italy .................. 23105 A/88

[51] Int. Cl.$^5$ .................. H01L 21/00; H01L 21/02; H01L 21/60; G01N 27/46
[52] U.S. Cl. .................. 437/40; 437/41; 357/25; 324/71.5; 204/416; 204/418
[58] Field of Search .................. 437/40, 41; 324/71.5; 357/25; 204/416, 418

[56] References Cited

U.S. PATENT DOCUMENTS

| | | | |
|---|---|---|---|
| 4,218,298 | 8/1980 | Shimada et al. | 204/418 |
| 4,236,987 | 12/1980 | Schindler et al. | 204/418 |
| 4,269,682 | 5/1981 | Yano et al. | 357/25 |
| 4,505,799 | 3/1985 | Baxter | 437/40 |
| 4,735,702 | 4/1988 | Reinhoudt et al. | 204/418 |
| 4,874,499 | 10/1989 | Smith et al. | 357/25 |
| 4,878,015 | 10/1989 | Schmidt et al. | 324/71.5 |

Primary Examiner—Brian E. Hearn
Assistant Examiner—B. Everhart
Attorney, Agent, or Firm—Shea & Gould

[57] ABSTRACT

A process for obtaining a multifunctional, ion-selective-membrane sensor is disclosed, which process comprises the following steps:

a) preparation of a siloxanic prepolymer, followed by one or more deposition(s) of said siloxanic prepolymer on a device of MOS or ISFET type;

b) preparation of a solution containing an ionophore, a monomer of a polymerisable olefin, 2,4-toluenediisocyanate and a dialcohol or a diamine or a glycol or a trialcohol or a triamine, which preparation is followed, after that said solution has been kept stirred for at least 48 hours at room temperature, by the deposition thereof on the siloxanic prepolymer, which deposition is carried out by means of a spinner;

c) photochemical treatment in the presence of a photo-initiator by means of UV light, with a suitable mask being used, which allows the exposure to UV light to take place on one gate only;

d) chemical washing of the sensor, by means of an organic solvent;

e) thermal treatment ("thermal curing"), so as to complete the reactions of polymerization;

f) preparation and deposition onto the siloxanic polymer of another solution, or of a plurality of other solutions, by operating in a similar way as of the above (b) step, which solution(s) contain(s) an ionophore different from the preceding one(s), which deposition is followed by the (c), (d) and (e) steps, with a mask being used, which is different from the preceding mask(s), which makes it possible for the exposure to UV light to be carried out on a gate different from the preceding one(s).

16 Claims, 5 Drawing Sheets

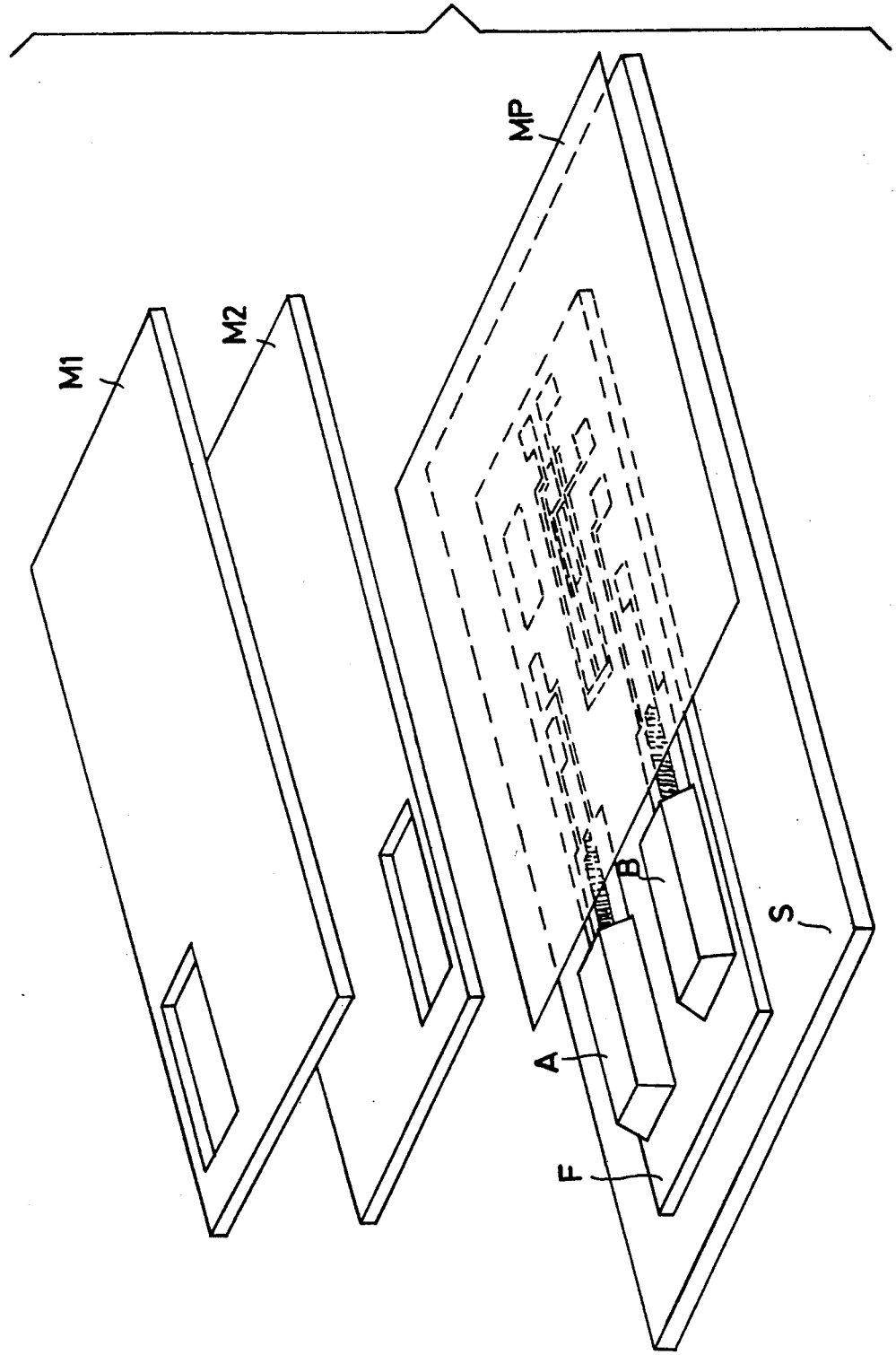

PROCESS FOR OBTAINING A MULTIFUNCTIONAL, ION-SELECTIVE-MEMBRANE SENSOR USING A SILOXANIC PREPOLYMER

FIELD OF THE INVENTION

The present invention relates to a process for obtaining a multifunctional, ion-selective-membrane, sensor (i.e., a "multiprobe").

BACKGROUND OF THE INVENTION

From the prior art, some solutions are known for the production of such multifunctional sensors, containing ion-selective or enzymatic membranes. A recently developed technique uses photolithography ("photopattern") (see. S. Nakamoto, N. Ito, T. Kirigama, J. Kimura: Sensors and Actuators—13, 1988, 165; Y. Hazanato, M. Nakako, M. Maede, J. Shicno: Anal. Chimica Acta, 193, 1987, 87).

BRIEF DESCRIPTION OF THE DRAWINGS

FIG. 3 is an exploded view of a multiprobe according to the invention.

In FIG. 1, a general process of this type is schematically shown, which uses a photoresist.

Figure 1A:
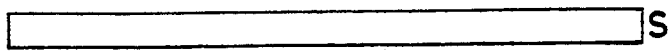
FIG. 1 is a graphic depiction of a process for production of a multiprobe according to the prior art.
Figure 1B:
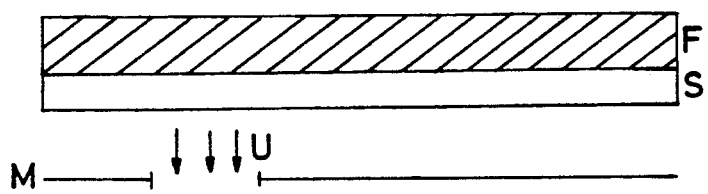

Onto a substrate (S) [FIG. 1(a)], a photoresist (F) is applied by means of a spinner [FIG. 1(b)].

Figure 1C:
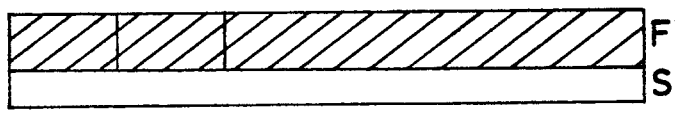
Figure 1D:
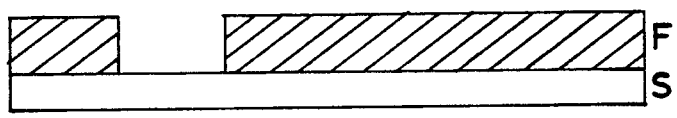

By means of a mask (M), a photochemical treatment is carried out with UV light (U) [FIG. 1(c)] and after a subsequent development with a proper solution, a hollow is thus formed, inside which the membrane will be deposited [FIG. 1(d)].

Figure 1E:
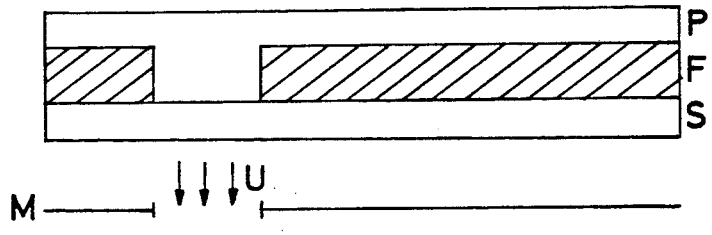
Figure 1F:
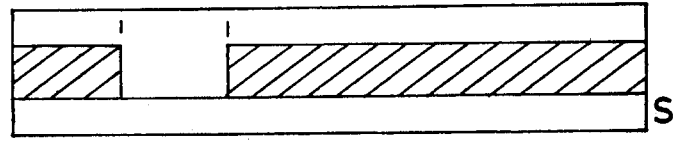
Figure 1G:
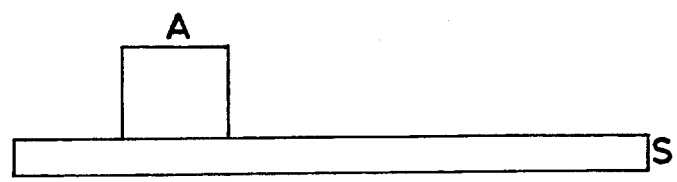

The membrane (P) is then deposited by means of a spinner [FIG. 1(e)], and a second photochemical treatment [FIG. 1(f)] is carried out, which second photochemical treatment is followed by a lift-off process, or by a process of washing with solvents, and by a thermal treatment, with the ion-selective membrane (A) being obtained [FIG. 1(g)].

Figure 1H:
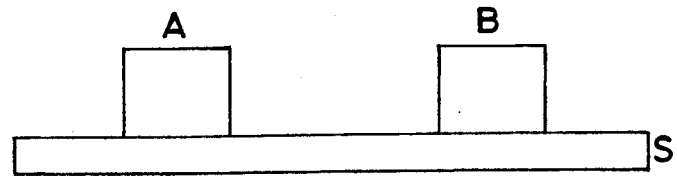

By repeating the steps from (b) to (g), using a reverse "mask" relatively to the first one, a second ion-selective membrane (B) is obtained [FIG. 1(h)].

The present Applicant has found now a process, which shows advantages as compared to the above described technique, which process uses a polymeric membrane, of the type as already disclosed and used in the U.S. patent application No. 07/221,436 filed 7/19/88 to the same applicant.

Among the advantages, the following can be listed:

the simplicity of use and preparation by using a spinner;

the chemical-physical characteristics of the polymeric material from which the membrane is made, are very similar to those of a photoresist, but with the possibility of operating in white light and not only in the dark, or in yellow light, as required by the use of the same photoresist;

the polymeric material which is obtained is bonded by means of chemical bonds to the silanized surface of the gate of the FET with reactive groups, whilst in case of use of membranes as photoresist, such chemical bonds are not formed;

finally, the number of process steps is lower than as needed when a photoresist is used.

SUMMARY OF THE INVENTION

The process according to the present invention for obtaining a multifunctional, ion-selective-membrane, sensor, which sensor is essentially constituted by a device based on semiconductors of MOS (Metal Oxide Semiconductor) type or of ISFET type (ISFET is an acronym standing for In Selective Field Effect Transistor), containing silicon oxide on its surface, and having two or more gates, and by two or more ioncphores, different from one another, with each one of said ionophores being entrapped inside a polymeric organic matrix based on a polymer obtained by means of the reaction between a polymerized olefin, the monomer of which has the formula:

$$HOZ^I - \underset{\underset{R^V}{|}}{C} = CH_2$$

wherein:

$Z^I$ is equal to

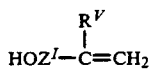

or to

wherein:

r is an integer which can have values of from 1 to 10; and $R^V$ can be either H or $CH_3$, with the value of $CH_3$ being excluded when $Z^I$ is equal to $(CH_2)_r$, and a compound obtained by means of the reaction between 2,4-toluene-diisocyanate and a dialcohol or a diamine or a glycol or a trialcohol or a triamine having the following formula:

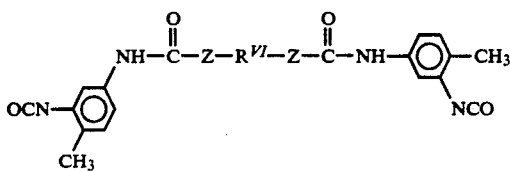

wherein:

$R^{VI}$ is equal to:

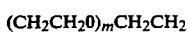

wherein
m is an integer which can have values comprised within the range of from 1 to 20,000;
or $R^{VI}$ is equal to $$(CH_2)_s$$

wherein
s is an integer which can have values comprised within the range of from 1 to 20,
or $R^{VI}$ is equal to:

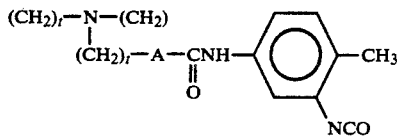

wherein:
t is an integer which can have values comprised within the range of from 1 to 10, and
Z can be either —NH— or —O—, with the value of —NH— being excluded when $R^{VI}$ is equal to:

$$(CH_2CH_2O)_mCH_2CH_2$$

with the silicon oxide being bonded to said polymeric organic matrix through a polysiloxanic matrix capable or chemically reacting with the polymeric matrix, is characterized in that said process comprises the following steps:

a) preparation of a siloxanic prepolymer, followed by one or more deposition(s) of said siloxanic prepolymer on a device of HOS or ISFET type;
b) preparation of a solution containing an ionophore, a monomer of a polymerisable olefin, 2,4-toluenediisocyanate and a dialcohol or a diamine or a glycol or a trialcohol or a triamine, which preparation is followed, after that said solution has been kept stirred for at least 48 hours at room temperature, by the deposition thereof on the siloxanic prepolymer, which deposition is carried out by means of a spinner;
c) photochemical treatment in the presence of a photoinitiator which makes it possible an olefinic monomer to be polymerised by means of UV light, with bonds $$(-C-C-)_{n^I}$$

being formed, wherein $n^I$ is an integer which can have a value comprised within the range of from 100 to 10,000, with a suitable mask being used, which allows the exposure to UV light to take place on one gate only;
d) chemical washing of the sensor, by means of an organic solvent;
e) thermal treatment ("thermal curing"), so as to complete the reaction of polymerization;
f) preparation and deposition onto the siloxanic polymer of another solution, or of a plurality of other solutions, by operating in a similar way as of the above (b) step, which solution(s) contain(s) an ionophore different from the preceding ionophore(s), which deposition is followed by the (c), (d) and (e) steps, but with a mask being used, which is different from the preceding mask(s).

DETAILED DESCRIPTION OF THE PREFERRED EMBODIMENTS

The polysiloxanic matrix can be preferably selected from among the organosilanes of general formula

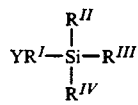

wherein
$R^{II}$, $R^{III}$, $R^{IV}$, which can be either equal to, or different from, one another, are alkyl or alkoxy groups containing from 1 to 10 carbon atoms, and
$R^I$ is equal to $$(CH_2)_pX(CH_2)_q,$$

wherein
X is $CH_2$ or a monocondensed or polycondensed aromatic group or NH or O, and
p and q, which can be either equal to, or different from, each other, are integers which can have values comprised within the range of from 0 to 10, with the value of zero being excluded when X is either NH or O,
Y is —$NH_2$ or —OH or —SH.

In that case, the structure obtained from the polysiloxanic matrix from the polymeric organic matrix and from the silicon oxide existing on the surface of the MOS or ISFET device can be schematically represented as follows:

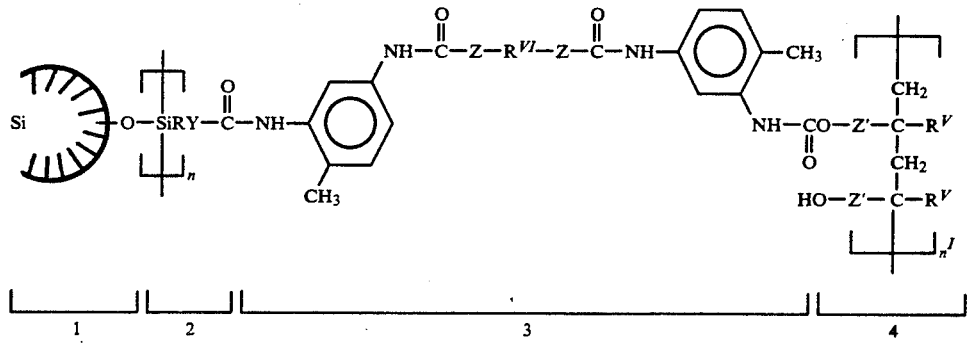

In case $R^{VI}$ is equal to

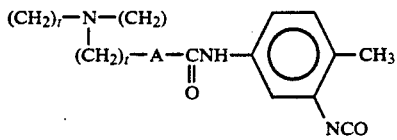

the third isocyanate function will form a linkage with a further moiety as above indicated by the numeral 4, with a higher level of crosslinking being obtained in the polymer (n and n' are integers which can have values comprised within the range of from 100 to 10,000).

By means of the above reference numerals, the following are indicated:
by 1 silicon oxide;
by 2 the polysiloxanic matrix;
by 3 the polymeric organic matrix on the basis of 2,4-toluene-diisocyanate;
by 4 the polymeric matrix based on a polymerized olefin.

As polysiloxanic matrices, for exemplifying purposes, aminoethylaminopropyltrimethoxysilane (AEAPS) or aminoethylaminomethylphenetyltrimethoxysilane (AEAMPS) or 3-aminopropyltriethoxysilane can be used.

As ionophores, organic molecules with an open structure (such as, e.g., of the type of ETH 227, ETH 1001, ETH 1644, and so forth), or with a cyclic structure (such as of the type, e.g., of Valinomycin, the crown-ethers, the cryptands, and so forth), can be used. The device of MOS type, besides the presence of silicon oxide and, possibly, silicon nitride, on its surface, should contain in its portion under the same silicon a layer of aluminum or gold, deposited by evaporation.

For example, as the polymeric organic matrix, hydroxyethylmethacrylato and a compound obtained by means of the reaction of 2,4-toluene-diisocyanate and triethyleneglycol or triethanolamine, can be used. The depositions of the siloxanic prepolymer and of the solution containing the constitutents of the membrane and the ionophore, can be carried out by means of the so-said "spin-on" techniques, i.e., by using a rotary-disk equipment. The excess of so-deposited solution is removed by centrifugation, owing to the revolutionary movement of the disk. Then, the solvent of the solution evaporates and the compound(s) in question polymerize(s) and react(s) under the thermal and photochemical effect.

The thermal treatments of the siloxanic prepolymer and of the solution containing the components of the selective membrane deposited on the polysiloxanic layer are preferably carried out at a temperature comprised within the range of from 40° to 200° C., and preferably comprised within the range of from 80° to 150° C.

The photochemical treatment, by means of the use of UV light, is carried out, e.g., by means of a mercury-vapour lamp (type HBO 100/W2). The deposited thickness of siloxanic prepolymer should be comprised within the range of from 0.1 to 10 μm, and should be preferably comprised within the range of from 0.5 to 3 μm, and the deposited thickness of the membrane-containing solution should be comprised within the range of from 0.1 to 100 m, and preferably comprised within the range of from 10 μ to 30 μm.

The revolution speed (revolutions per minute, rpm) at which the depositions by means of spin-on devices are carried out, should be comprised within the range of from 500 to 6000, and preferably of from 3500 to 5500, rpm.

The deposition of the siloxanic prepolymer on substrates of silicon or of silicon oxide of devices of MOS or ISFET type, can be carried out by plasma-deposition, preferably under the following conditions:
power comprised within the range of from 20 to 50 W;
discharge pressure comprised within the range of from 0.1 to 1 torr;
temperature comprised within the range of from room temperature, up to the temperature of decomposition of the siloxanic prepolymer used.

EXAMPLES

The purpose is of directly obtaining on a semiconductor device functionalized with reactive organosilanes, regions coated by selective membranes, and regions without said membranes.

In this regard, some examples are reported in the following for the purpose of better illustrating the invention without however limiting it.

For examplifying purposes, the modality for depositing and producing two membranes with different selectivities—in that they contain different ionophores—is disclosed.

Example 1 llustrates the process for depositing two ion-selective membranes not into contact with each other, and Example 2 illustrates the process for depositing two membranes into contact with each other along one side.

The advantage of the process of Example 2 is that during the step of preparation of the sensor, such a process does not require the use of a sealant between the two membranes.

EXAMPLE 1

Example 1 is schematically illustrated in the flow diagram of FIG. 2. The starting substrate is a FET device (i.e., a "Field Effect Transistor").

On a dual-gate FET device withous contacts, containing two membrane gates, of 2.3 mm×3.1 mm of dimensions, the following operations are carried out:

Mechanical masking of the region of the contacts existing on the device, by means of a suitable, special adhesive tape resistant to heat and to the photochemical treatment;

Deposition on the gate of a solution (M) containing an organosilane patially hydrolysed in an alcoholic medium, after that the solution is left standing for 48 hours at room temperature. The starting solution is constituted by:
21% of 3-[(2-aminoethyl)-amino]-propyl-trimethoxysilane
3% of acetic acid
1% of water
in absolute ethanol.

The deposition is carried out by means of a rotary-disk device at 5000 rpm for 30 seconds (spin-coating). A precuring of siloxane at 150° C. for 20 minutes can be optionally carried out.

In FIG. 1(a) the silanized FET (F) is shown, which has two gates (the source and the drain of each gate are represented as small rectangles of black colour).

Figure 2A:
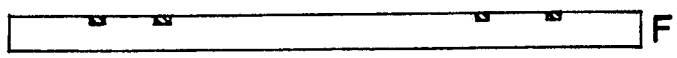
FIG. 2 is a graphic depiction of a process for production of a multiprobe according to the present invention, wherein two ion-selective membranes are not in contact with each other.
Figure 2B:
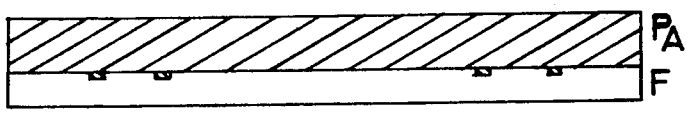

Deposition [FIG. 2(b)] of a slightly viscous solution (P$_A$), obtained as follows:

The solution is prepared, which contains the diisocyanate-based compound, obtained as follows:

| | |
|---|---|
| tetrahydrofuran | 2 ml |
| 2,4-toluene-diisocyanate | 1.5 ml |
| triethyleneglycol | 0.7 ml | and the solution is kept with stirring for 72 hours at the temperature of 25° C.

To this solution:

| | |
|---|---|
| 2-hydroxyethyl methacrylate | 2 ml | is added, and the so obtained solution is kept stirred for about 8 hours at the temperature of 25° C.

To 1 ml of this so-obtained solution, 30 mg of Valinomycin ia product by FLUKA), and 1% of 2,2-diethoxyacetophenone, to be used as the photoinitiator, are added.

The deposition is carried out by means of a spin-coating technique, by operating at 5000 rpm for 30 seconds. The deposition process is repeated twice.

Figure 2C:
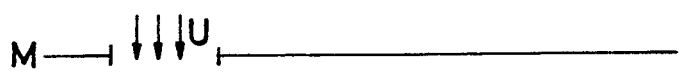

Exposure [FIG. 2(c)] to UV light (U), with the use of a mask (M), which makes it possible the exposure to UV light to take place on one only of the two gates of the FET device (i.e., on the first gate).

The device is exposed to the effect of UV light for a time of 5 minutes, with the UV lamp being kept at a distance of about 25 cm from the samples. In this way, the complete polymerization of methacrylate is only obtained in the region left uncovered by the mask.

Washing of the device with acetone in an ultra-sound bath, for a few minutes.

The device is subsequently submitted to a treatment of thermal type at 110° C. for a time of 8 hours. In this way, the complete condensation is obtained between the —OH groups of the methacrylate and of the aminosilane, with the —NCO groups of the compound obtained by means of the reaction of toluenediisocyanate with triethyleneglycol. Furthermore, the complete polymerization of the pre-hydrolised organosilane, and the reaction of the alkoxide groups with the —SiOH groups of sil con oxide take place.

Figure 2D:
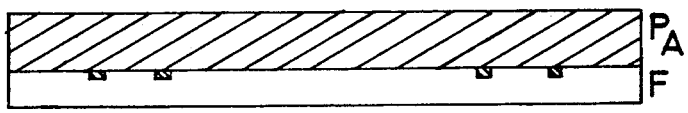

Now, a device with one gate coated by an ion-selective membrane (A) [FIG. 2(d)] has been obtained.

In order to deposit and produce a second membrane on the same device, the following procedure is used.

Figure 2E:
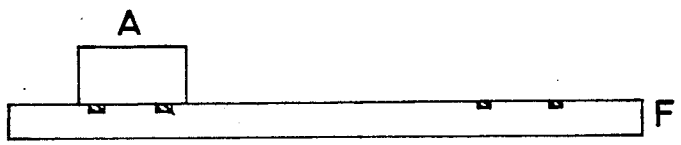

On the same device already containing the first membrane, selective for K+, the following steps are carried out:

Deposition [FIG. 2(e)] of a slightly viscous solution ($P_B$), obtained as follows:

The solution is prepared, which contains the diisocyanate-tased compound, obtained as follows:

| | |
|---|---|
| tetrahydrofuran | 2 ml |
| 2,4-toluene-diisocyanate | 1.5 ml |
| triethyleneglycol | 0.7 ml | and the solution is kept with stirring for 72 hours at the temperature of 25° C.

To this solution:

| | |
|---|---|
| 2-hydroxyethyl methacrylate | 2 ml | is added, and the so obtained solution is kept stirred for about 8 hours at the temperature of 25° C.

To 1 ml of this so-obtained solution, 30 mg of an ionophore different from Valinomycin, such as, e.g., Nonactin, selective for $NH_4+$ and 1% of 2,2-diethoxyacetophenone, to be used as the photoinitiator of methacrylate polymerization, are added.

The deposition is carried out by means of a spin-coating technique, by operating at 5000 rpm for 30 seconds. The deposition process is repeated twice.

Figure 2F:
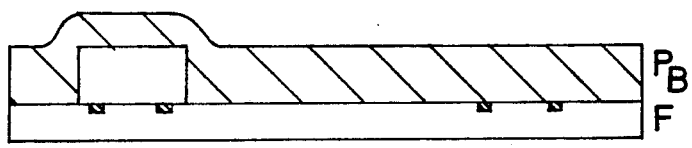
Figure 2G:
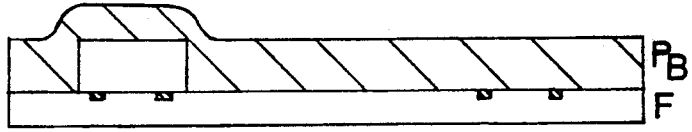

Exposure [FIG. 2(f)] to UV light (U), with the use of a mask (M), which makes it possible the exposure to UV light to take place on the second gate only.

The device is exposed to the effect of UV light for a time of 5 minutes, with the lamp being kept at a distance of about 25 cm from the samples. In this way, the complete polymerization of methacrylate is obtained.

Washing of the device with acetone in an ultra-sound bath, for a few minutes.

The device is subsequently submitted to a second treatment of thermal type at 110° C. for a time of 8 hours. In this way, the complete condensation is obtained between the —OH groups of the methacrylate and of the aminosilane, with the —NCO groups of the compound obtained by means of the reaction of toluenediisocyanate with triethyleneglycol. Furthermore, the complete polymerization of the prehydrolised organosilane, and the reaction of the alkoxide groups with the —SiOH groups of silicon oxide take place [FIG. 2(g)].

FIG. 3 shows the result which can be obtained on a dual-gate FET, wherein:
M1: Mask 1
M2: Mask 2
F: Dual-gate FET
S: Support
MP: Adhesive protecting mask
A: Membrane 1
B: Membrane 2

Figure 4:
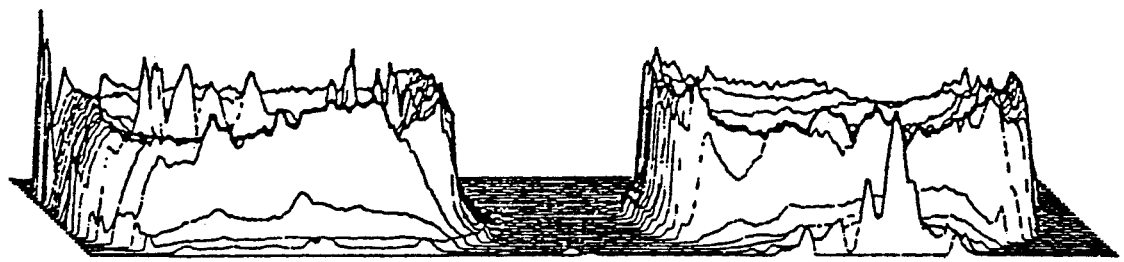
FIG. 4 is a microspectrofluorimeter profile of a glass-type substrate obtained according to the present invention.

FIG. 4 shows the result obtained according to this process on a silanized substrate of glass type.

Figure 5:
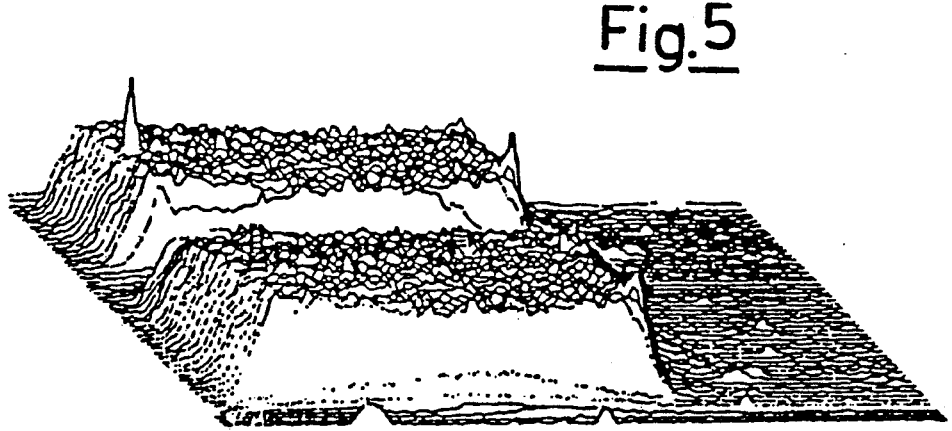
FIG. 5 is microspectrofluorimeter profile of an oxidized and silanized silicon substrate obtained according to the present invention.
Figure 6A:
FIG. 6 is a graphic depiction of a process for production of a multiprobe according to the present invention, wherein two ion-selective membranes are in contact with each other.
Figure 6B:
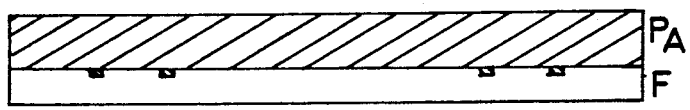
Figure 6C:
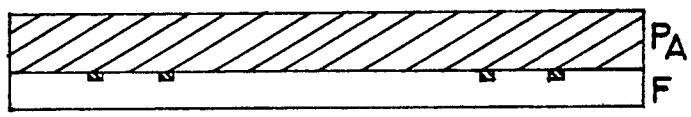
Figure 6D:
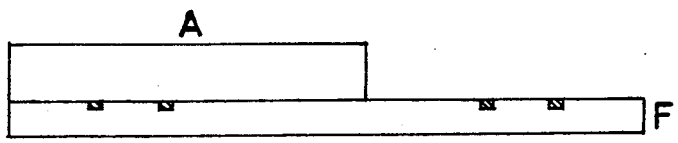
Figure 6E:
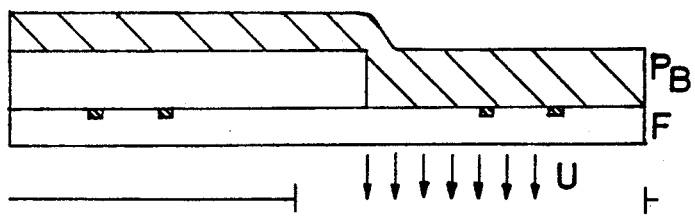
Figure 6F:
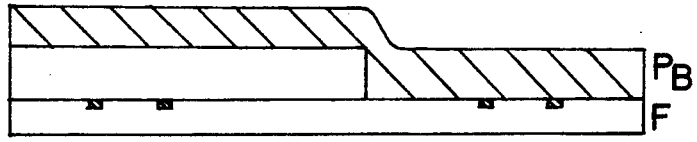
Figure 6G:
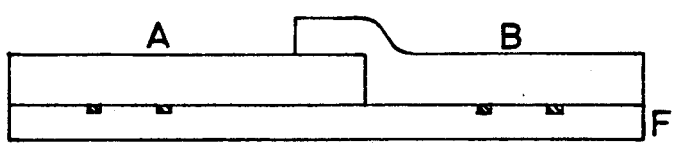
Figure 6H:
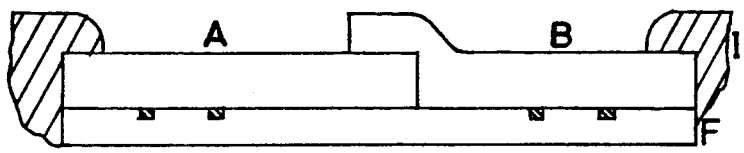

FIG. 5 shows the result obtained according to this process on an oxidated and silanized silicon substrate.

The profile shown in FIGS. 4 and 5 was obtained by exploiting the effect of fluorescence of the polymeric material, as recorded by means of a microspectrofluorimeter. In FIGS. 3, A and B are, as said, polymeric membranes chemically bonded to the device, with selectivities for different ions, in that they contain different ionophores.

Figure 2H:
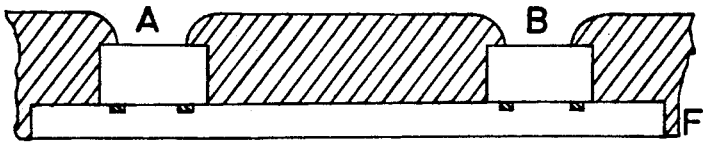

Then, in order to prepare the complete sensor, in case of FET, tie following operations have to be carried out:

Mechanical removal of the adhesive layer used in order to act as the mask for the deposition of the membrane;

Housing of the device on a commercial metal support of $TO_5$ type;

Installation of the contacts for connection with the device on the support, by means of the use of an ultrasound microwelder;

deposition of a suitable sealant (I) on the device provided with the contacts, and on the support, without touching any of the two polymeric membranes [FIG. 2(h)].

EXAMPLE 2

The same procedure as of Example 1 is followed, as schematically shown in the flow diagram of FIG. 6; the end result is that two membranes with different selectivity are produced, partially superimposed to each other on one side only.

This result is achieved by using two masks with a wider opening, in order that the polymerization of both the first and the second membrane can take place on a larger surface area.

The flow diagram of FIG. 6 is analogous to that of FIG. 3; the only variations are the opening is wider [FIG. 3(c), (f)] and the resulting overlapping [FIG. 3(h)].

We claim:

1. A process for obtaining a multifunctional, ion-selective-membrane sensor wherein the sensor comprises a device having semiconductors of MOS or ISFET types, containing silicon oxide on its surface, and having two or more active-regions gates, and two or more ionophores, different from one another, with each one of said ionophores entrapped inside a polymeric organic matrix based on a polymer obtained by means of the reaction between a polymerized olefin, the monomer having the formula:

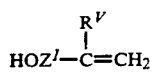

wherein:

$Z^I$ is equal to

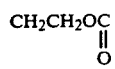

or to

wherein:

r is an integer having values of from 1 to 10; and $R^V$ is either H or $CH_3$, with the value of $CH_3$ being excluded when $Z^I$ is equal to $(CH_2)_r$, and a compound obtained by means of the reaction between 2,4-toluene-diisocyanate and a dialcohol or a diamine or a glycol or a trialcohol or a triamine having the following formula:

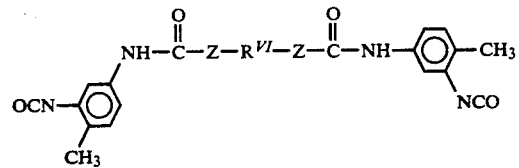

wherein:

$RV_I$ is equal to:

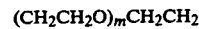

wherein m is an integer having values comprising a range of fropm 1 to 20,000; or $RV_I$ is equal to

wherein s in an integer having values comprising a range of from 1 to 20, or $R^{VI}$ is equal to:

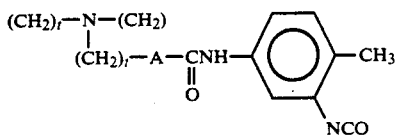

wherein:

t is an integer having values comprising a range of from 1 to 10, and

Z is either —NH— or —O—, with the value of —NH— being excluded when $R^{VI}$ is equal to:

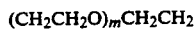

with the silicon oxide being bonded to said polymeric organic matrix through a polysiloxanic matrix capable or chemically reacting with the polymeric matrix, wherein the process comprises the following steps:

a) preparing a siloxanic prepolymer, followed by one or more deposition(s) of said siloxanic prepolymer on a device of MOS or ISFET-type;

b) preparing a solution containing an ionophore, a monomer of a polymerizable olefin, 2,4-toluene-diisocyanate and a dialcohol or a diamine or a glycol or a trialcohol or a triamine, which preparation is followed, after that said solution has been kept stirred for at least 48 hours at room temperature, by the deposition thereof on the siloxanic prepolymer, which deposition is carried out by means of a spinner;

c) photochemical treatment in the presence of a photoinitiator for making an olefinic monomer to be polymerized by means of UV light with bonds

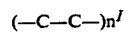

being formed, wherein $n^I$ is an integer which can have a value comprising a range of from 100 to 10,000, with a suitable mask being used, which allows the exposure to UV light to take place on one gate only;

d) chemically washing the sensor, by means of an organic solvent;

e) thermal treatment for completing the reaction of polymerization;

f) preparation and deposition onto the siloxanic polymer of another solution, or of a plurality of other solutions, by operating in a similar way as of the above (b) step, which solution(s) contain(s) an ionophore different from the preceding ionophore(s), which deposition is followed by the (c), (d) and (e) steps, with a mask being used, which is different from the preceding mask(s).

2. The process of claim 1, wherein the siloxanic prepolymer is deposited by means of a rotary disk device.

3. The process of claim 1, wherein the siloxanic prepolymer is deposited by plasma-deposition.

4. The process of claim 3, wherein the plasma-deposition is at a power comprising a range of from 10 to 100 W, and under a discharge pressure comprising a range of from 0.1 to 1 torr.

5. The process of claim 2 or 3, wherein the siloxanic prepolymer is carried out in such a way, as form a layer, is deposited for forming a layer having a thickness comprising a range of from 0.1 to 10 μm.

6. The process of claim 1, wherein the solutions containing the ionophore, the monomer of the polymerizable olefin, 2,4-toluene-diisocyanate and the dialcohol or the triamine are deposited by means of a rotary-disk device.

7. The process of claim 1, wherein the solution is deposited onto the siloxane prepolymer for producing a layer having a thickness comprising a range of from 0.1 to 100 μm.

8. The process of claim 2 or 6, wherein the rotary-disk device operates at a revolution speed comprising a range of from 500 to 600 revolutions per minute (rpm).

9. The process of claim 1, wherein the ionophores from among the organic molecules ETH 227 ™, ETH 10001 ™, ETH 1644 ™ having an open structure, or among the organic molecules Valinomycin ™, the crown-ethers, or the cryptands having a cyclic structure.

10. The process of claim 1, wherein the thermal treatment occurs at a temperature comprising a range of from 40' to 200° C.

11. The process of claim 10, wherein the temperature of the thermal treatment comprises a range of from 40° to 200° C.

12. The process of claim 1, wherein the polysiloxanic matrix is selected from among the organosilanes of general formula

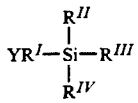

wherein
$R^{II}$, $R^{III}$, $R^{IV}$, can be either equal to, or different from, one another, are alkyl or alkoxy groups containing from 1 to 10 carbon atoms, and
$R^{I}$ is equal to

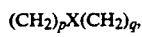

wherein
X is $CH_2$ or a monocondensed or polycondensed aromatic group or NH or O, and
p and q, can be either equal to, or different from each other, and are integers having values comprising a range of from 0 to 10, with the value of zero being excluded when X is either NH or O, and
Y is $-NH_2$ or $-OH$ or $-SH$.

13. The process of claim 1, wherein the polysiloxanic matrix is aminoethylaminopropyltrimethoxysilane (AEPS) or aminoethylaminomethylphenetyltrimethoxysilane (AEAPS), or 3-aminopropyltriethoxysilane.

14. The process of claim 5, wherein the deposition of the siloxane prepolymer is for forming a layer having a thickness comprising a range of from 0.5 μm to 3 μm.

15. The process of claim 7, wherein the deposition of the solution onto the siloxanic prepolymer is for producing a layer having a thickness comprising a range of from 10 μm to 30 μm.

16. The process of claim 8, wherein the rotary disk operates at a revolution speed comprising the range of from 3500 to 5500 revolutions per minute.

* * * * *